(12) United States Patent
Henderson

(10) Patent No.: US 8,932,656 B1
(45) Date of Patent: Jan. 13, 2015

(54) OIL BLEND FOR SKIN TREATMENT

(76) Inventor: Aja Henderson, North Plainfield, NJ (US)

( * ) Notice: Subject to any disclaimer, the term of this patent is extended or adjusted under 35 U.S.C. 154(b) by 21 days.

(21) Appl. No.: 13/594,008

(22) Filed: Aug. 24, 2012

Related U.S. Application Data

(60) Provisional application No. 61/536,723, filed on Sep. 20, 2011.

(51) Int. Cl.
| | |
|---|---|
| *A61K 36/889* | (2006.01) |
| *A61K 36/28* | (2006.01) |
| *A61K 36/48* | (2006.01) |
| *A61K 9/70* | (2006.01) |
| *A61K 31/355* | (2006.01) |
| *A61K 36/36* | (2006.01) |
| *A61K 36/53* | (2006.01) |
| *A61K 36/61* | (2006.01) |
| *A61K 36/63* | (2006.01) |

(52) U.S. Cl.
CPC ............ *A61K 36/889* (2013.01); *A61K 31/355* (2013.01); *A61K 36/28* (2013.01); *A61K 36/36* (2013.01); *A61K 36/53* (2013.01); *A61K 36/61* (2013.01); *A61K 36/63* (2013.01)
USPC ............ 424/764; 424/727; 424/757; 424/449

(58) Field of Classification Search
CPC ..... A61K 36/28; A61K 36/61; A61K 36/889; A61K 31/355; A61K 2800/31; A61K 9/282
See application file for complete search history.

(56) References Cited

U.S. PATENT DOCUMENTS

| | | | |
|---|---|---|---|
| 4,454,159 A | 6/1984 | Musher | |
| 4,784,849 A * | 11/1988 | Tutsky | 424/73 |
| 5,578,312 A * | 11/1996 | Parrinello | 424/401 |
| 6,627,178 B1 | 9/2003 | Cauthon | |
| 6,716,441 B1 | 4/2004 | Osborne | |
| 7,115,287 B2 | 10/2006 | Froggartt | |
| 7,241,456 B2 | 7/2007 | Vromen | |
| 7,357,950 B2 | 4/2008 | Mazzio | |
| 7,390,507 B2 | 6/2008 | Ruwart | |
| 7,879,344 B2 | 2/2011 | Feldcamp | |
| 2002/0044977 A1 | 4/2002 | Close | |
| 2004/0081681 A1 * | 4/2004 | Vromen | 424/449 |
| 2004/0175343 A1 | 9/2004 | Osborne | |
| 2008/0145443 A1 | 6/2008 | Langolf | |
| 2008/0206155 A1 | 8/2008 | Tamarkin | |
| 2008/0233060 A1 | 9/2008 | Grune | |
| 2008/0234224 A1 | 9/2008 | Kamachi | |
| 2008/0311234 A1 | 12/2008 | Yoneda | |
| 2009/0123504 A1 | 5/2009 | Feldkamp | |
| 2010/0247563 A1 | 9/2010 | Hines | |
| 2010/0303854 A1 | 12/2010 | Hines | |
| 2011/0008474 A1 | 1/2011 | Boegli | |
| 2011/0097279 A1 | 4/2011 | Tamarin | |
| 2011/0136210 A1 | 6/2011 | Benjamin | |

FOREIGN PATENT DOCUMENTS

WO    WO 2010006376 A1 *   1/2010

OTHER PUBLICATIONS

Bedi et al. (2002) Arch Dermatol. vol. 138. p. 232-242.*
Aburjai et al. (2003) Phytother. Res. 17, 987-1000.*
Hempel (1999) Acta Hort. 503: 15-20.*
Priest, D. Medicinal and Aromatic Plants—Industrial Profiles. (1999), 9, (Tea Tree), 203-206. Publisher: (Harwood Academic Publishers).*
Lee et al. (2010) J. Vet. Sci. 11(1): 35-41.*

* cited by examiner

*Primary Examiner* — Chris R Tate
*Assistant Examiner* — Russell Fiebig
(74) *Attorney, Agent, or Firm* — CreatiVenture Law; Linda L. Lewis

(57) ABSTRACT

A blend of oils for treating or preventing skin ailments, such as diaper rash and eczema and for soothing the skin. The blend includes virgin coconut oil, extra virgin olive oil, jojoba oil, calendula oil, vitamin E oil, tea tree oil, German chamomile extract. The vitamin E is essentially free from corn oil and soy oil.

11 Claims, No Drawings

OIL BLEND FOR SKIN TREATMENT

CROSS-REFERENCE TO RELATED APPLICATIONS

This application claims the benefit of provisional patent application No. 61,536,723 filed Sep. 20, 2011.

STATEMENT REGARDING FEDERALLY SPONSORED RESEARCH

Not Applicable.

APPENDIX

Not Applicable.

BACKGROUND OF THE INVENTION

1. Field of the Invention

The present invention is directed to a unique blend of oils for treating and soothing skin.

2. Related Art

Diaper dermatitis or diaper rash is a condition where the stratum corneum is attacked and the skin is irritated and inflamed. The commonly known factors linked to diaper dermatitis include ammonia, bacteria, the products of bacterial actions, enzymes, pH, candida albicans and moisture. The diaper dermatitis is principally initiated by prolonged and repeated exposure to urine and feces under occlusive condition such as the micro-environment created by wearing an absorbent article. Under such condition, the skin may get overhydrated, leading to diminished barrier function. The friction and rubbing with the absorbent article create further damages to the skin. Thus, the skin becomes more susceptible to the irritants such as those in the urine or feces. While this condition is certainly more common in infants, it is not limited to infants. Similar conditions occur in, for example, incontinent or bed-ridden adults. Furthermore, similar skin irritation may occur from repeated wiping/chaffing of sensitive skin.

Since there are multiple factors linked to diaper dermatitis, the practical approach attempts to address the multiple causes and/or important cofactors. For example, reducing skin hydration by frequent changing of diapers, the use of moisture absorbing powders, the use of superabsorbent materials, and improving air flow in diapers are well known approaches. The use of artificial barriers (e.g., ointments, lotions) is also widely practiced.

Typically, a topical cream, ointment, lotion or paste is applied to the skin under the absorbent article by hand to provide some degree of physical barrier protection against bodily exudates or irritants. For the topical application method to be effective, the creams or ointments need to be substantive, i.e., they need to coat the target surface and remain at the site of application. Most current topical delivery systems are O/W or W/O (oil in water or water in oil) emulsions. These emulsions generally have inferior solubility properties, hence they are easily removed by moisture (from washing, perspiration or other bodily exudates), or rubbing against clothing, and often fail to provide long-lasting benefits to the site of application. These water-containing emulsions are particularly unsuitable for overhydrated skin such as is under an absorbent article.

Water-free creams or ointments are also known. Typically, these creams or ointments use oleaginous base such as petrolatum to provide the substantively of the creams or ointments for a long-lasting coating of the target areas.

Less common delivery systems are substantially anhydrous, oleaginous compositions. The oleaginous compositions are generally more water insoluble than the O/W or W/O emulsions; thus, they may serve as reservoirs from which the active ingredients are continuously delivered. However, they may not be efficient in delivering the water soluble active ingredients. This is because the skin care actives are water-soluble and exist as solid particles or powders in the oleaginous composition. These solid particles or powders are entrapped in the substantially anhydrous oleaginous base and cannot be easily released from the composition to the target skin surface. Moreover, even when these active ingredients are in contact with the target skin surface, they may not function efficiently in their solid form.

The present invention is directed to a substantially anhydrous of blend of oils for treating and soothing skin that overcomes the disadvantages of the related art compositions. Because the claimed composition is a mixture of oils, it resists removal with water or bodily fluids. Since there are no water-soluble actives in the oil blend, there is no failure of the composition in delivering the drug active. The unique blend of oils provides soothing of irritated skin with anti-bacterial and anti-fungal actives that are readily available to heal the skin.

SUMMARY OF THE INVENTION

The present invention is directed to a substantially anhydrous blend of oils comprising coconut oil, tea tree oil, vitamin E, and German chamomile extract, wherein the blend does not contain water soluble actives. Substantially anhydrous means that at 70 degrees F., there is no separate water phase visible in the blend. To not contain water soluble actives means that at 70 degrees F., there are no visible particles of water soluble actives present in the blend. In an embodiment of the invention, the blend of oils comprises virgin coconut oil, extra virgin olive oil, jojoba oil, calendula oil, vitamin E oil, tea tree oil, German chamomile extract. Preferably, the vitamin E is essentially free from corn oil and soy oil.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses. The preferred ingredients used in this blend of oils are pure and organic. As different blends were made and tested this was found to be critical to the effectiveness of the desired blend. Tea tree oil and lavender oil are considered anti-bacterial. Coconut oil and tea tree oil are considered anti-fungal. Olive oil, jojoba oil and calendula oil are considered soothing to the skin. It is taught that German chamomile extract provides mild pain relief. Vitamin E is thought to promote healing. Grapefruit seed extract is used as an antibacterial additive, however, the grapefruit seed extract caused burning of the skin when applied, so it was removed from the oil blend.

Coconut oil is thought to be anti-fungal and therefore the primary component. Coconut oil is solid below 74 degrees F. and a solid or semi-solid mixture was undesirable. The blend was varied to maximize the amount of coconut oil while keeping the mixture a liquid at room temperature. It was determined that up to about 40 vol. % coconut oil could be used without the blend solidifying, which in turn resulted in separation. Below about 70 degrees F., the product did begin to solidify, but no separation was observed. Above about 70 degrees F., the blend is liquid and homogeneous. A preferred range of coconut oil is from about 20 to 45 vol. %. A more preferred range is from about 30 to 40 vol. %.

The remaining approximately 60 vol. % of the mixture can be made up of extra virgin olive oil, jojoba oil, calendula oil, vitamin E oil, tea tree oil and German chamomile extract. The extra virgin olive oil, jojoba oil and calendula oil act as carriers for the other oils and are therefore optional. However, adding one or more of them to the blend does provide a product that is easier to handle and store. In an embodiment, the extra virgin olive oil is present from about 0 to 30 vol. %, the jojoba oil is present from about 0 to 30 vol. % and the calendula oil is present from about 0 to 30 vol. %. In a preferred embodiment, equal amounts of olive oil, jojoba oil and calendula oils produced the best results.

Tea tree oil is widely renowned as being anti-bacterial but can be irritating if applied directly to the skin directly, so very small amounts are used in the oil blend. The preferred concentration is from about 0.01 vol. % to about 1.0 vol. %. Lavender oil was added for its antibacterial properties and also for its fragrant smell, and was added from about 0 to 5.0 wt. %. Baby products may contain lavender because it has a calming effect on infants. German chamomile extract was also added at about 0.1 vol. % to 5.0 vol. % and vitamin E was added at 0.1 vol. % to 10.0 vol. %. The German chamomile extract would provide pain relief and the vitamin E would help heal the skin while the other ingredients fought the cause of the rash.

Vitamin E was used but found to be less effective than a preferred all natural vitamin E that was essentially free of corn oil and soy oil. A commercial source of such oil is UNIQUE E a trademark of A.C. Grace and sold by Vitamin Shoppe. A preferred vitamin E formula is devoid of all fillers, additives, wheat, gluten, corn oil or soy oil. The preferred vitamin E contains d-alpha tocopherol. Oil blends made with the vitamin E essentially free of corn oil and soy oil were very effective in treating diaper rash, even diaper rash caused by yeast.

This blend of oils is suitable for soothing and treating skin. It is particularly considered efficacious in treating or preventing diaper rashes, including yeast-caused rashes. It is also suitable for treating or preventing skin rashes such as eczema, dry skin or other skin conditions.

The oil is used by applying directly to the skin with rubbing or massaging. For treating diaper rash, the oil should be applied and re-applied to the skin at each diaper change until the rash is healed.

The following examples are for illustrative purposes only and in no way limit the scope of the invention.

| Example 1 | |
|---|---|
| Component | Volume |
| Organic Unrefined Virgin Coconut Oil | 2 parts/400 mL |
| Extra Virgin Olive Oil | 1 part/200 mL |
| Organic Jojoba Oil | 1 part/200 mL |
| Calendula Oil | 1 part/200 mL |
| A.C. Grace Vitamin E Oil | 3% by volume/30 mL |

| -continued | |
|---|---|
| Example 1 | |
| Component | Volume |
| 100% Tea Tree Oil | 1 drop per 10 mL/10 mL |
| Lavender Oil | 1 drop per 10 mL/10 mL |
| German Chamomile Extract in Jojoba Oil | 1 drop per 10 mL/10 mL |

| Example 2 (Lavender Free) | |
|---|---|
| Component | Volume |
| Organic Unrefined Virgin Coconut Oil | 2 parts/400 mL |
| Extra Virgin Olive Oil | 1 part/200 mL |
| Organic Jojoba Oil | 1 part/200 mL |
| Calendula Oil | 1 part/200 mL |
| A.C. Grace Vitamin E Oil | 3% by volume/30 mL |
| 100% Tea Tree Oil | 1 drop per 10 mL/10 mL |
| German Chamomile Extract in Jojoba Oil | 1 drop per 10 mL/10 mL |

The above-listed ingredients were warmed above 70 degrees F. and mixed together. The oils were substantially anhydrous and the mixture, when cooled to about 70 degrees F. was liquid and homogeneous. There were no visible particles due to water soluble actives. When applied to skin with diaper rash, the rash cleared up in a few days.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A topical skin-soothing composition consisting essentially of an effective amount of a substantially anhydrous blend of oils consisting of:
   about 38 vol. % unrefined virgin coconut (*Cocos nucifera*) oil,
   about 19 vol. % extra virgin olive oil,
   about 19 vol. % jojoba (*Simmondsia chinensis*) oil,
   about 19 vol. % calendula oil
   about 1 vol. % tea tree (*Melaleuca*) oil
   about 0.1 to 1.0 vol. % German chamomile (*Matricaria chamomilla*) extract, and
   about 0.1 to 1.0 vol. % mixed tocopherol oil;
   wherein the mixed tocopherol oil is free of soy and corn oils, and wherein the composition does not contain water-soluble actives.

2. A topical skin-soothing composition consisting essentially of an effective amount of a substantially anhydrous blend of oils consisting of:
   about 38 vol. % unrefined virgin coconut (*Cocos nucifera*) oil,
   about 19 vol. % extra virgin olive oil,
   about 19 vol. % jojoba (*Simmondsia chinensis*) oil,
   about 19 vol. % calendula oil
   about 1 vol. % tea tree (*Melaleuca*) oil
   about 1 vol. % lavender oil about 0.1 to 1.0 vol. % German chamomile (*Matricaria chamomilla*) extract, and
about 0.1 to 1.0 vol. % mixed tocopherol oil;
wherein the mixed tocopherol oil is free of soy and corn oils, and wherein the composition does not contain water-soluble actives.

3. The composition of claim 1, wherein the composition is liquid and homogenous at about 70 degrees F. or warmer.

4. A method of treating skin ailments and soothing skin comprising applying to the skin of a subject in need thereof an effective amount of the composition of claim 1.

5. A method of treating skin ailments and soothing skin comprising applying to the skin of a subject in need thereof an effective amount of the composition of claim 2.

6. The method of claim 4, wherein the blend is liquid and homogenous at about 70 degrees F. or warmer.

7. The method of claim 4, wherein the skin ailment is diaper rash.

8. The method of claim 4, wherein the skin ailment is eczema.

9. The method of claim 7, wherein the diaper rash includes a yeast infection.

10. The method of claim 7, wherein the topical composition is applied each time the diaper is changed until the rash disappears.

11. The method of claim 9, wherein the topical composition is applied each time the diaper is changed until the rash disappears.

* * * * *